United States Patent [19]

Rinehart, Jr. et al.

[11] Patent Number: 4,948,791
[45] Date of Patent: Aug. 14, 1990

[54] NOVEL CYTOTOXIC CYCLIC DEPSIPEPTIDES FROM THE TUNICATE TRIDIDEMNUM SOLIDUM

[75] Inventors: Kenneth L. Rinehart, Jr.; Ryuichi Sakai, both of Urbana, Ill.; Justin G. Stroh, Stonington, Conn.

[73] Assignee: The Board of Trustees of the University of Illinois, Urbana, Ill.

[21] Appl. No.: 335,903

[22] Filed: Apr. 10, 1989

[51] Int. Cl.$^5$ .................. A61K 31/395; C07D 521/00
[52] U.S. Cl. ...................................... 514/183; 540/455
[58] Field of Search .......................... 540/455; 514/183

[56] References Cited

U.S. PATENT DOCUMENTS

4,668,669  5/1987  Barriere et al. ...................... 540/455

Primary Examiner—Robert T. Bond
Attorney, Agent, or Firm—Saliwanchik & Saliwanchik

[57] ABSTRACT

Novel didemnin compounds named didemnin X and didemnin Y have been isolated from the Caribbean tunicate *Trididemnum solidum*. These compounds have cytotoxic activity and, therefore, are useful as antitumor drugs.

6 Claims, 9 Drawing Sheets

FIG. IE

| | $R_1$ | $R_2$ | $R_3$ |
|---|---|---|---|
| 5 |  | H | CH₃CHOHC(O)– |

FIG. IF

| | $R_1$ | $R_2$ | $R_3$ |
|---|---|---|---|
| 6 |  | H | H |

FIG. IG

| | $R_1$ | $R_2$ | $R_3$ |
|---|---|---|---|
| 7 |  | H |  |

FIG. IH

| | $R_1$ | $R_2$ | $R_3$ |
|---|---|---|---|
| 8 |  | H |  |

FIG. II

| | $R_1$ | $R_2$ | $R_3$ |
|---|---|---|---|
| 9 |  | H |  |

FIG. IJ

| | $R_1$ | | |
|---|---|---|---|
| 11 |  | $R_2 + R_3 = CH_2$ | |

| | NATURAL | | SYNTHETIC | |
|---|---|---|---|---|
| | R₁ | R₂ | R₁ | R₂ |
| 14. | H | H | 15a. | H | CH₃ |
| 14a, | H | CH₃ | 16a. | Rx | CH₃ |
| 14b, | Rx | CH₃ | 17a, | Ry | CH₃ |

| | SYNTHETIC | |
|---|---|---|
| | R₁ | R₂ |
| 15b, | H | CH₃ |
| 16b, | Rx | CH₃ |
| 17b, | Ry | CH₃ |

DIDEMNIN X(1): SOLID, mp 156-158°C, [α]$_D$= -88.6° (CHCl$_3$)

FIG. IS

DIDEMNIN Y (2): [α]$_D$= -65° (CHCl$_3$)

NOVEL CYTOTOXIC CYCLIC DEPSIPEPTIDES FROM THE TUNICATE TRIDIDEMNUM SOLIDUM

This invention was made with government support under grant A1 04769 awarded by the Department of Health and Human Services. The government has certain rights in this invention.

BACKGROUND OF THE INVENTION

Didemnins, antitumor and antiviral cyclic depsipeptides, were initially isolated in 1981 from the Caribbean tunicate *Trididemnum sodium* (Rinehart Jr., K. L., J. B. Gloer, J. C. Cook Jr., S. A. Misak, T. A. Scahill [1981] J. Am. Chem. Soc. 103:1857). So far, nine related peptides, didemnins A (3), B (4), C (5), nordidemnins A (6), and B (7), didemnins D (8), E (9), G (10), and methylene didemnin A (11) have been characterized (Rinehart Jr., K. L., J. B. Gloer, R. G. Hughes Jr., H. E. Renis, J. P. McGovren, E. B. Swynenberg, D. A. Stringfellow, S. L. Kuentzel, L. H. Li [1981] Science 212:933; Gloer, J. B. [1983] Ph. D. Dissertation, University of Illinois at Urbana-Champaign; Gutowsky, R. E. [1984] M. Sc. Thesis, University of Illinois at Urbana-Champaign). See FIGS. 1, 1A, 1B, and 1C for the structural formulas of the bold face compound numbers referred to herein. Didemnin A (3) is the simplest and most abundant constituent, and it consists of five amino acid and two non-amino acid subunits. The structure of one of the non-amino acid subunits, (3S,4R,5S)-isostatine, was originally assigned as (3S,4R)-statine, but was later found to be incorrect, and it was revised during the synthetic study of 3 (Rinehart, K. L., V. Kishore, S. Nagarajan, R. J. Lake, J. B. Gloer, F. A. Bozich, K.-M. Li, R. E. Maleczka Jr., W. L. Todsen, M. H. G. Munro, D. W. Sullins, R. Sakai [1987] J. Am. Chem. Soc. 109:6846; Rinehart, K. L., V. Kishore, K. C. Bible, R. Sakai, D. W. Sullins, K.-M. Li [1988] J. Nat. Prod. 51:1; Sakai, R., First Year Paper I, University of Illinois at Urbana-Champaign). Of the didemnins isolated so far, 4 has shown the most potent biological activities, and strong antitumor efficacy has led this compound into Phase II clinical trials. Structurally, all didemnins except for nor- and methylene didemnins contain 3 as the basic skeleton, and the only differences between them are their side chains. Differences in the side chain or simple modifications in the ring functional groups, however, cause drastic changes in their biological properties (Gloer [1983], supra). These interesting structure-activity relationships stimulated us to find new didemnins for further chemical and biological studies. See U.S. Pat. No. 4,548,814, which discloses and claims processes for preparing didemnins A, B, and C, and nordidemnins A, B, and C. Also, see U.S. Pat. No. 4,493,796, which discloses and claims didemnins A, B, C, D, and E.

BRIEF SUMMARY OF THE INVENTION

Figure 1:
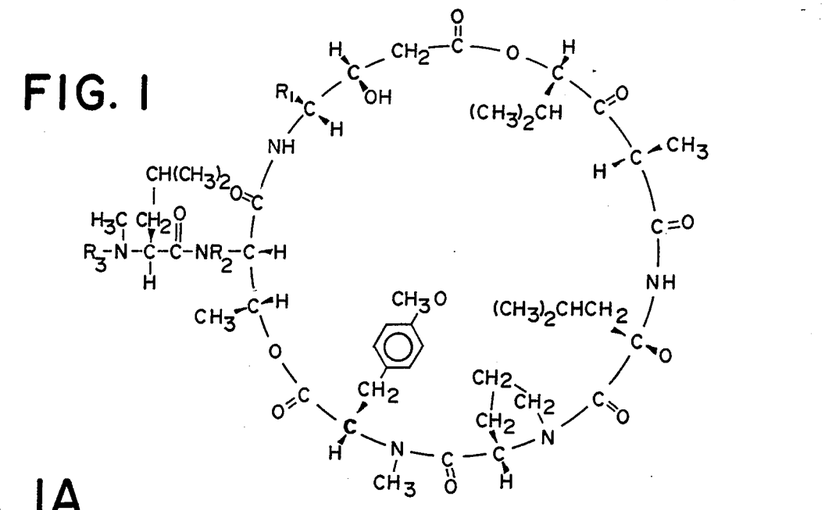
FIGS. 1 through 1T show the structural formulas of the bold-faced compound numbers.
Figures 1A, 1B:
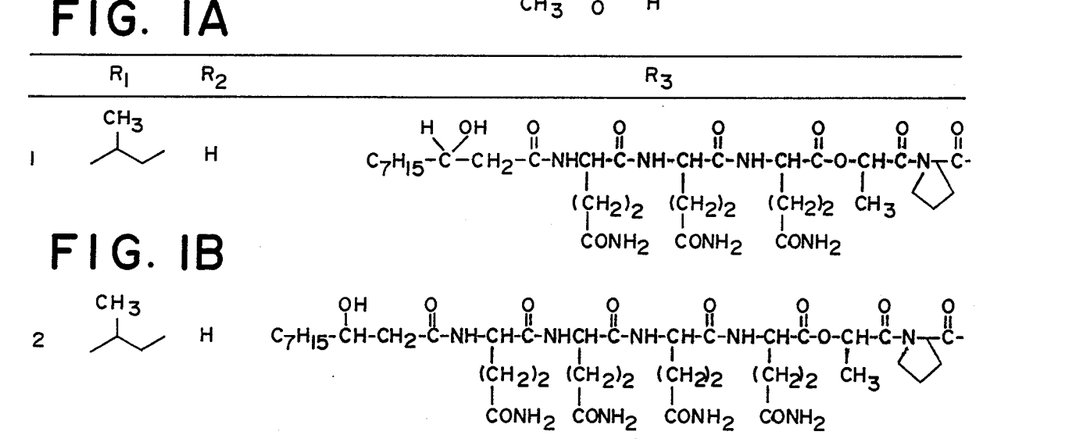
Figure 1C:
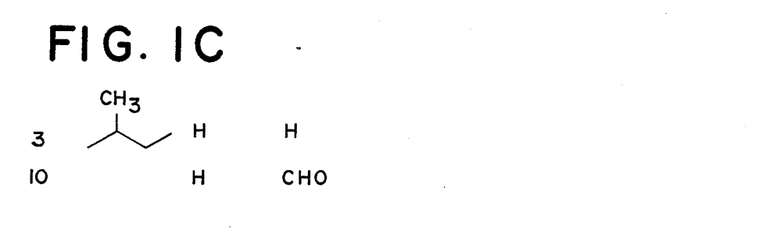
Figure 1D:
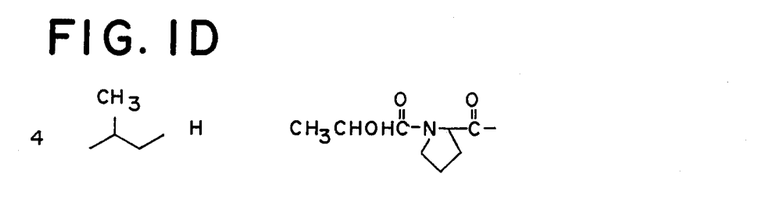
Figure 1E:
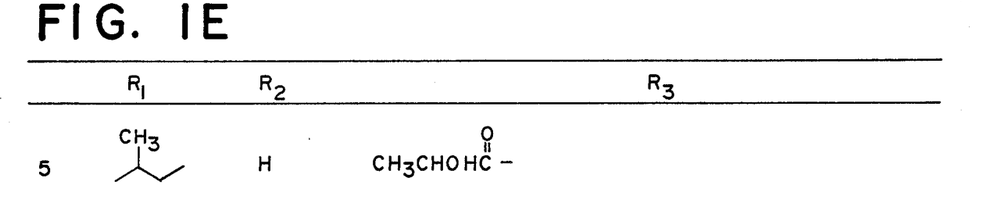
Figure 1F:
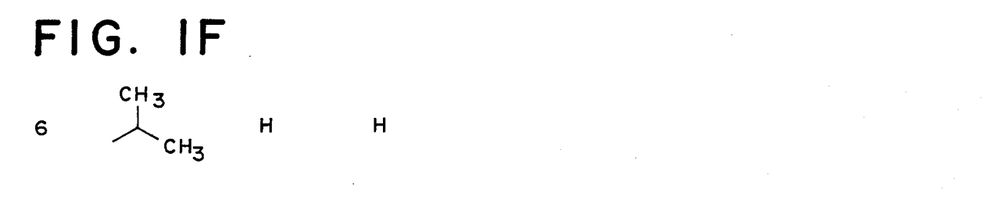
Figure 1G:
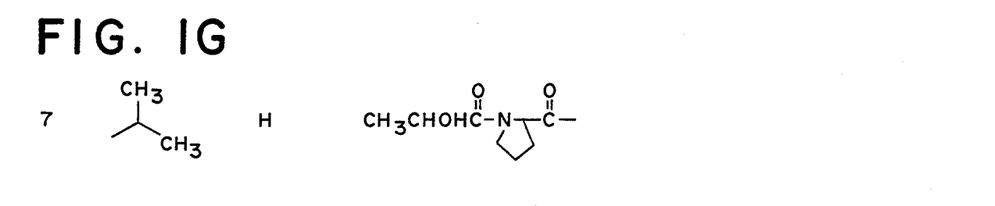
Figure 1H:
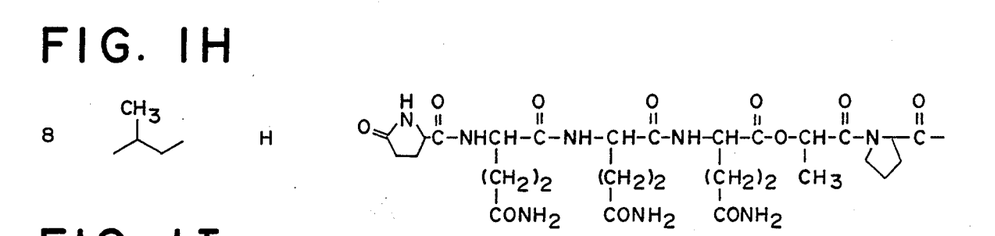
Figure 1I:
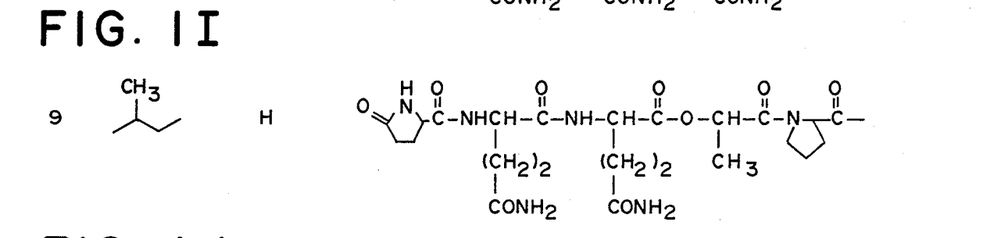
Figure 1J:
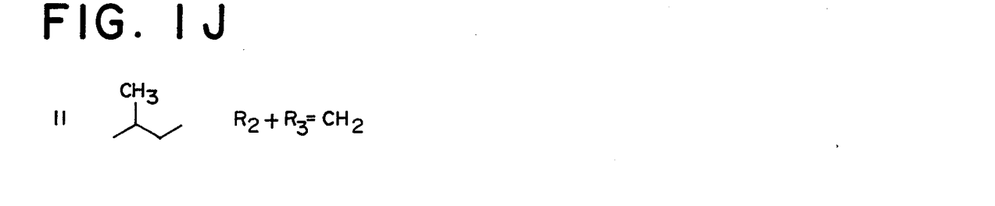
Figure 1K:
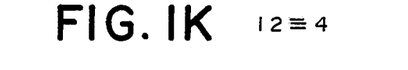
Figure 1L:
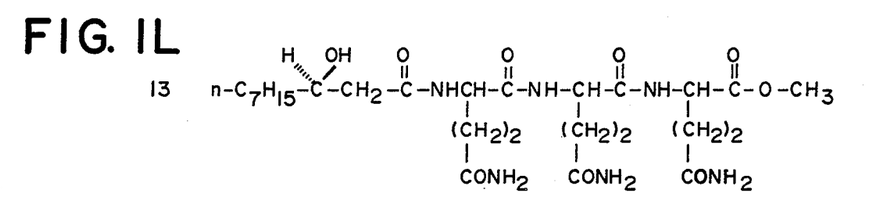
Figure 1M:
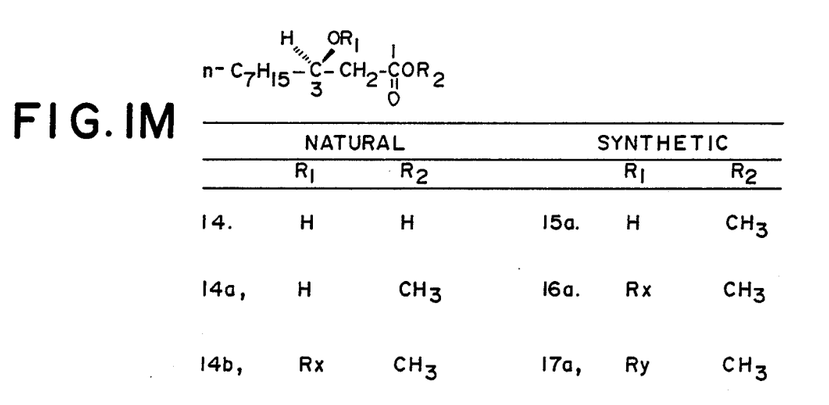
Figures 1N, 1O:
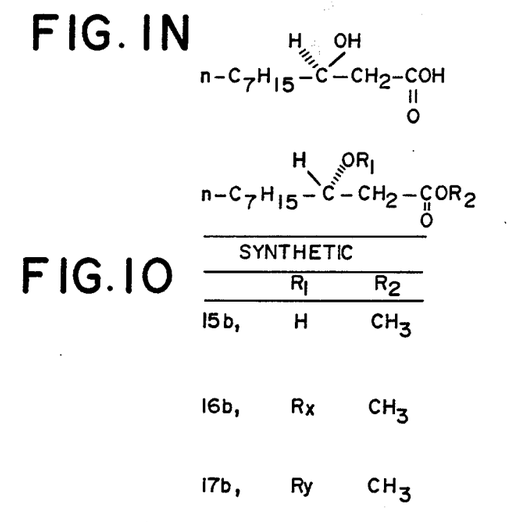
Figure 1P:
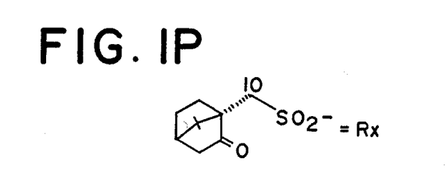
Figure 1Q:
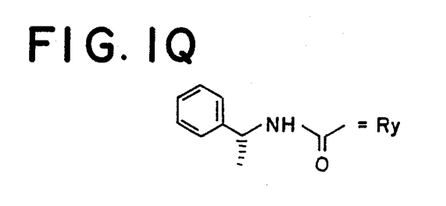
Figure 1R:
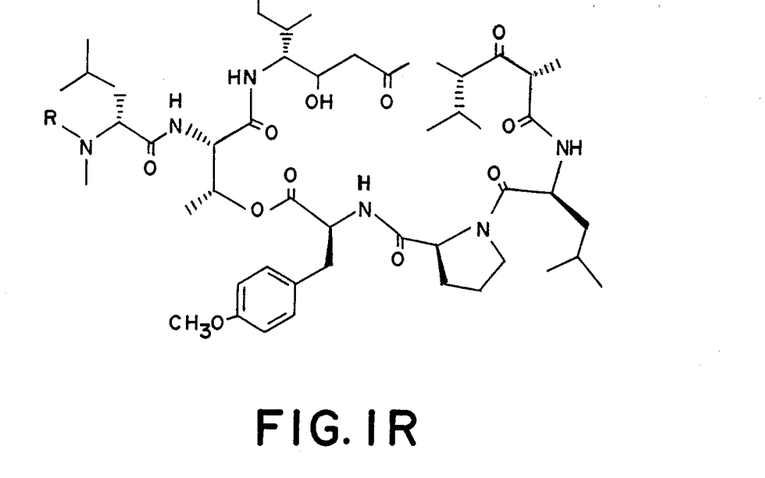
Figure 1S:
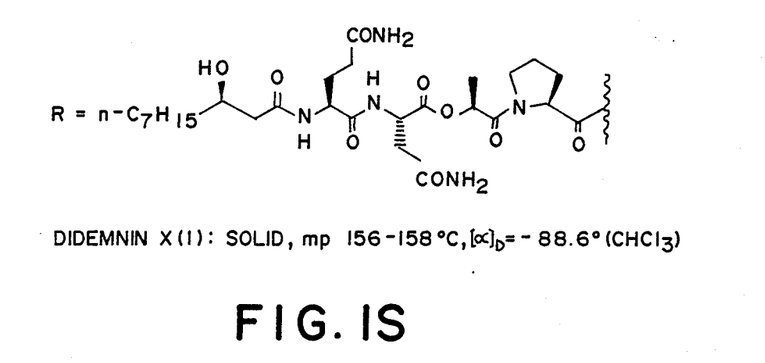
Figure 1T:
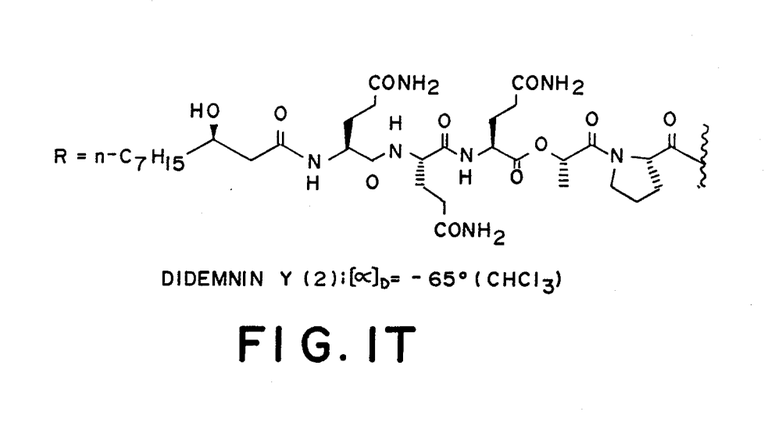
Figure 2A:
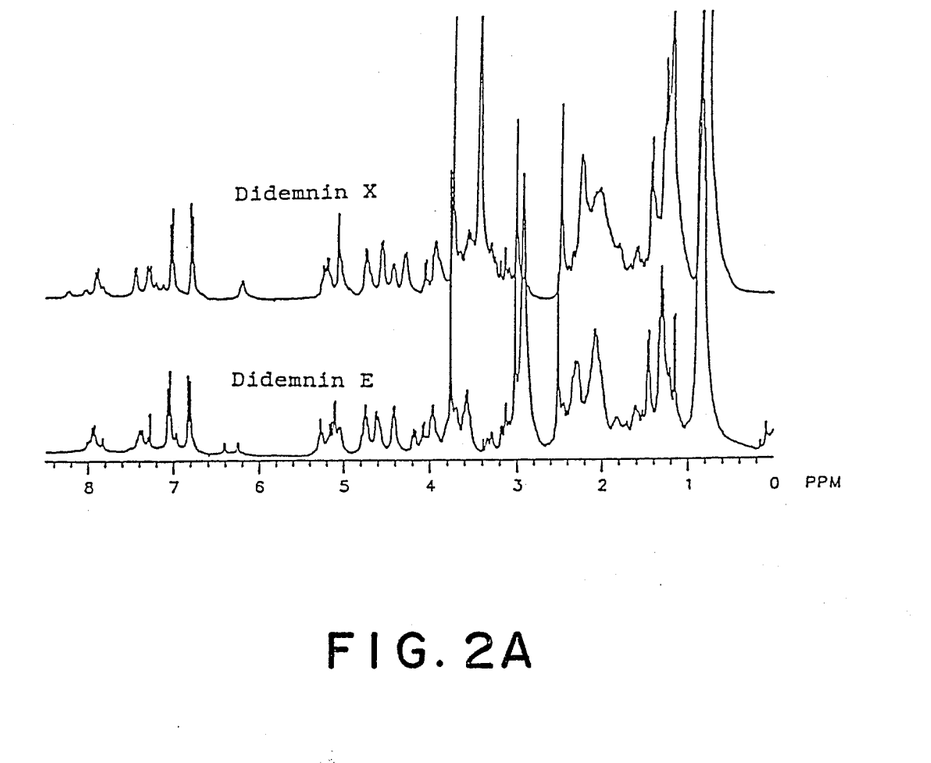
FIG. 2A and 2B and delete "X,E,Y, and D." and insert X (1) and E (9), Y (2), and D (8) in $CDCl_3$+Methanol-$d_4$ shows $^1H$ NMR data of didemnins X, E, Y, and D.
Figure 2B:
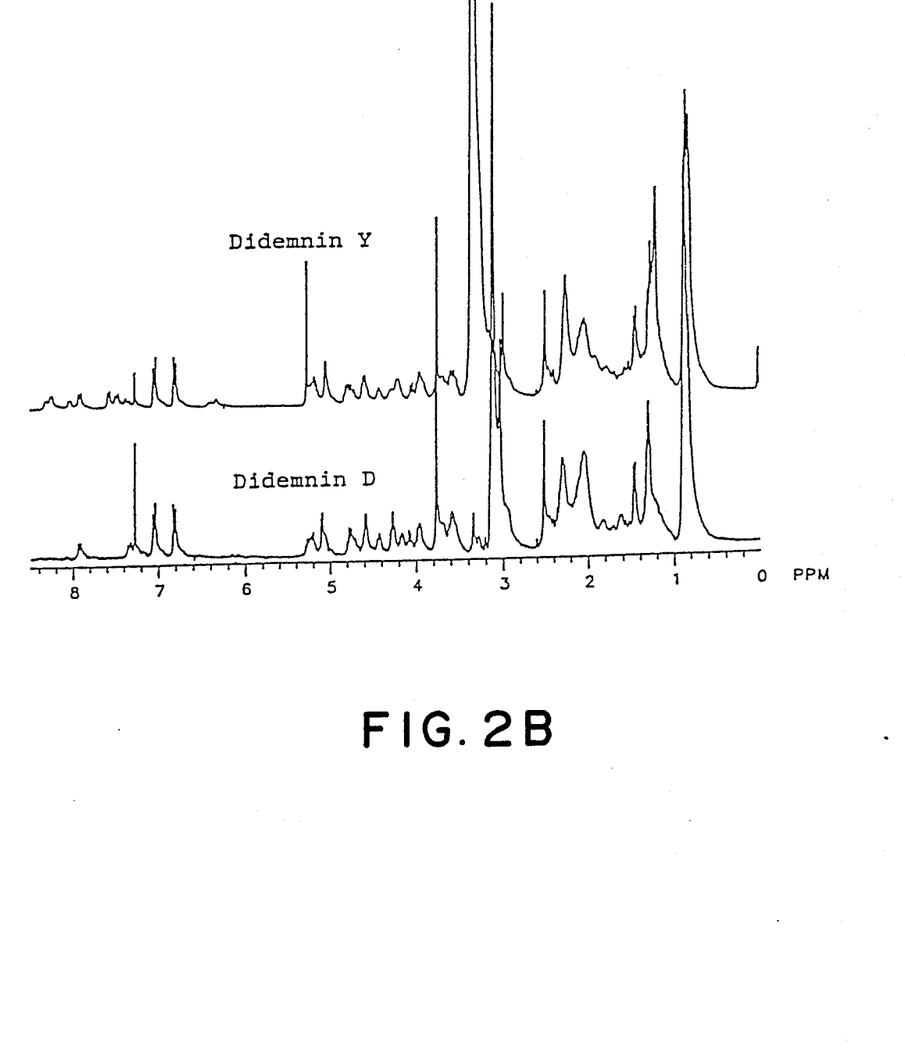

An extract of the marine tunicate *Trididemnum solidum* (Subphylum Urochordata) was chromatographed as shown in Scheme 1 to allow isolation of the new compounds, didemnins X (1) and Y (2). Their structures were elucidated by chemical and spectral methods, largely fast atom bombardment mass spectrometry (FABMS) and MS/MS studies, and are shown in FIG. 2. The absolute stereochemistry of the β-hydroxydecanoyl group was determined by comparison with synthetic material. As shown in Table 1, didemnins X and Y inhibit the growth of L1210 mouse leukemia cells in vitro.

TABLE 1

| Didemnin | Three-day L1210 cell growth inhibition assay (at 37° C.) | | | |
|---|---|---|---|---|
| | $ID_{50}$ ug/mL | $ID_{90}$ ug/mL | $ID_{50}$ ug/mL | $ID_{90}$ ug/mL |
| X | 0.004 | 0.017 | 0.0048 | 0.017 |
| Y | 0.0064 | 0.021 | 0.0048 | 0.02 |
| D | 0.0034 | 0.015 | 0.0042 | 0.016 |
| E | 0.0011 | 0.0076 | 0.0008 | 0.0056 |
| B | | | 0.0038 | 0.015 |
| A | 0.0078 | 0.058 | | |

Thus, these compounds can be used to treat neoplastic diseases in animals and humans. Further, since these novel compounds are active against DNA and RNA viruses, they can be used to treat infections in humans, animals, and plants that are caused by such viruses. Acid addition salts and acyl derivatives of the novel didemnins can be made and used for the same biological purposes as the parent compounds.

DETAILED DESCRIPTION OF THE INVENTION

The Organism

The organism from which didemnins (X and Y) are extracted is a colonial marine tunicate of the family Didemnidae, *Trididemnum solidum*. This is in the suborder Aplousobranchia of the order Enterogona of the class Ascidiacea of the subphylum Urochordata of the phylum Chordata. The animals can be readily obtained by scuba techniques at depths of 10 to 100 feet where they encrust rocks, sponges, gorgonians, etc., in colony sizes up to 3 feet in diameter and ½ inch in thickness. Depending on location, they are green-white to purple-white to brown-white to orange-white.

Specific locations from which these organisms have been obtained are as follows:

(1) Southwest side of Long Cay, Lighthouse Reef, Belize, 17° 11.8′ N by 87° 36.5′ W at a depth of 50 to 100 feet;

(2) Rada el Cove, Isla San Andres, Colombia, 12° 31′ 46″ N by 81° 44′ 5″ W at 25 to 33 feet;

(3) Palancar Reef, Isla de Cozumel, Mexico, 20° 18.2′ N by 87° 2.5′ W at 60 to 100 feet;

(4) On the west side of the southern tip of Turneffe Island, Belize, 17° 11.3′ N by 87° 55.6′ W at 50 to 75 feet;

(5) Punta Oeste, Coxen's Hole Harbor, Isla Roatan, Honduras, 16° 15′ N by 86° 38′ W at 10 to 70 feet;

(6) On the leeward side of the westernmost Holandes Cay, Isla San Blas, Panama, 9° 35.6′ N by 78° 47′ W at 60 feet.

Isolation and Purification of Didemnins X and Y

A variety of methods can be used to isolate and purify the didemnins and nordidemnins from samples of the tunicate organism, for example, solvent extraction, partition chromatography, silica gel chromatography, liquid-liquid distribution in a Craig apparatus, adsorption on resins, and crystallization from solvents.

Experimental Section

Infrared (IR) spectra were recorded on an IBM IR/32 FTIR. Optical rotations were measured with a Jasco DIP 360 digital polarimeter with a sodium lamp (589 nm) using a 5 cm (0.8 ml) cell. NMR spectra were obtained with a General Electric QE-300 instrument (300 MHz for $^1$H, 75 MHz for $^{13}$C). Chemical shifts are reported in ppm referenced to the chloroform peak at delta 7.26 ppm for $^1$H and 77.0 ppm for $^{13}$C, unless otherwise noted. High- and low-resolution (HR and LR) fast atom bombardment (FAB) mass spectra were measured by L. S. Rong on a VG Analytical ZAB. High- and low-resolution electron ionization (EI) mass spectra were measured by Dr. R. M. Milberg with a Finnigan MAT CH-5 DF spectrometer and a Finnigan MAT 731 instrument equipped with a multichannel signal analyzer. Melting points were determined on a Reichert microscope melting point apparatus and were not corrected. Gravity columns were prepared with commercial grade (Alfa large pore 58 micron) silica gel or NS gel (Nihon Seimitsu Kagaku, Tokyo; polystyrene divinyl benzene copolymer). High performance liquid chromatography (HPLC) was performed on a system containing an Altex model 110A pump, a Waters Associates R-401 differential refractometer, and a Beckman 153 UV detector. An Altex Ultrasphere silica (25 cm×0.4 cm, 5 m particle size) and Alltech Spherisorb C-18, phenyl, amino, or cyano columns (25 cm×1 cm, 5 or 10 m particle size) were used. A PC Inc. Ito multilayer coil separator-extractor was used for centrifugal counter current chromatography (CCC). Gas chromatography (GC) analyses were carried out by using a Varian Model 3700 GC and an Alltech Associate Inc., Chirasil-Val II capillary column (25 m×0.32 mm) at a flow rate of 1.2 mL/min with a programmed oven temperature [90° C.-(4° C./min)-180° C.].

During the large-scale isolation of 4, a large amount of polar fraction A was produced (Scheme I) (Gutowsky supra). From this fraction, didemnins D (8) and E (9), along with the novel tunichlorin pigments (Rinehart, Kishore, Bible et al. [1988] supra), have been isolated.

In the isolation of these new peptides, efficient solvent partition and centrifugal counter current chromatography (CCC) were used extensively to avoid potential loss and decomposition of polar components. A portion of fraction A (9 g) was partitioned between the upper and the lower phases of ethyl acetate/heptane/methanol/water (7:4:4:3). FABMS of the two phases indicated that the polar peptides were concentrated almost exclusively in the lower phase. The lower phase from the solvent partition was then separated by CCC with toluene/ethyl acetate/methanol/water (6:7:4:4) as the solvent system. The lower phase was used as a mobile phase to give crude didemnins D (8), E (9), Y (2), and X (1), 169 mg, 416 mg, 120 mg, and 248 mg, respectively, in order of elution. The crude peptides were purified by successive NS gel column chromatography, reversed phase, and normal phase HPLC to give the pure peptides.

Figure 3:
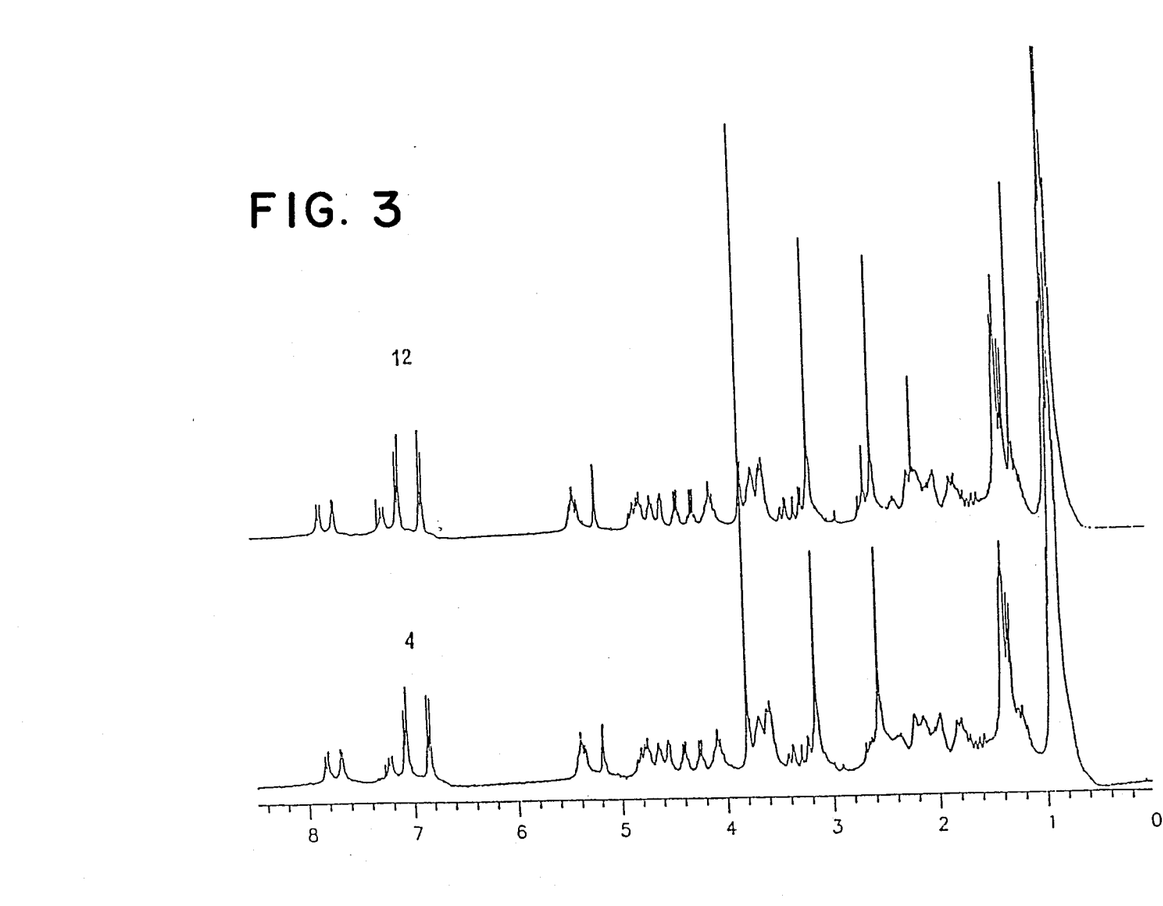
FIG. 3 shows $^1H$ NMR data of the methanolysis product of didemnin X, denoted "12", and didemnin B.

The molecular weight of 1 was deduced as $C_{82}H_{131}N_{13}O_{23}$ from HRFABMS. $^1$H and $^{13}$C NMR spectra of 1 and 2 were poorly resolved probably due to poor solubility and conformational inhomogeneity in the solution at room temperature. However, the complete spectral patterns of 1 and 2 were very similar to those of 4, 8, and 9 (FIGS. 1, 1A, 1B, and 1C), implying that 1 and 2 have the same basic skeleton as the other didemnins. Partial methanolysis of 1 gave 12 and 13 as the two major products. HRFABMS of 12 showed a molecular formula of $C_{57}H_{89}N_7O_{15}$, the same as that of 4. $^1$H NMR and optical rotation data of 12 were identical with those of authentic 4 (FIG. 3). Compound 13 has very poor solubility in common solvents except for DMSO and DMF, and $^1$H NMR signals of 13 in DMSO or DMF are very broad at room temperature. The molecular formula of 13 was deduced from HRFABMS data as $C_{26}H_{46}N_6O_9$, suggesting that 13 must be a methyl ester of the side chain of 1. LRFABMS data showed fragmentation ions at m/z 555.3, 427.3, 299.2, and 188.2, and HRFABMS of each fragment ion showed that 13 contains three glutamyl units and a terminal C-10 compound (Scheme II).

Figure 4:
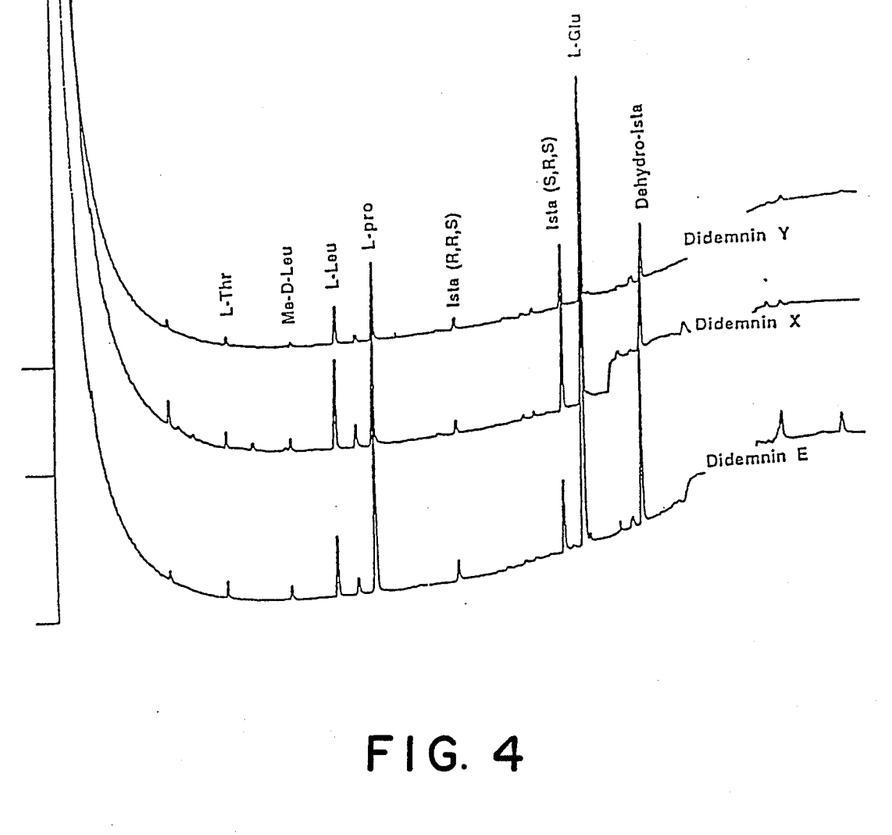
FIG. 4 shows chiral gas chromatographic data of didemnins X, Y, and E. Peak assignments were based on coinjection data. $Me_2Tyr$ is not identified in these data.

A comparison of chiral GC data of the hydrolyzates of 1 and 9 showed the amino acid composition of 1 to be exactly that of 9, including the absolute stereochemistry (FIG. 4).

Vigorous hydrolysis of 13 with 3N hydrochloric acid gave a lipophilic compound 14. The molecular formula of $C_{10}H_{20}O_3$ was determined by HRFABMS. $^1$H NMR spectra of 14, including decoupling experiments, along with HREI data of a fragment ion at m/z 89.023886 for the formula of $C_3H_5O_3^+$ (Scheme II) showed that the structure of 14 was 3-hydroxydecanoic acid. This was confirmed by comparison of $^1$H NMR data of 14 and its methyl ester 14a with those of synthetic (R,S)-3-hydroxydecanoic acid (15) and its methyl ester.

The absolute stereochemistry of 14a was determined by direct comparison of the $^1$H NMR data of the (+)-10-camphorsulfonyl derivative 14b with those of the synthetic methyl-3-(R)-and methyl-3-(S)-[(+)-10-camphorsulfonyl]decanoates, 16a and 16b, respectively.

Figure 5:
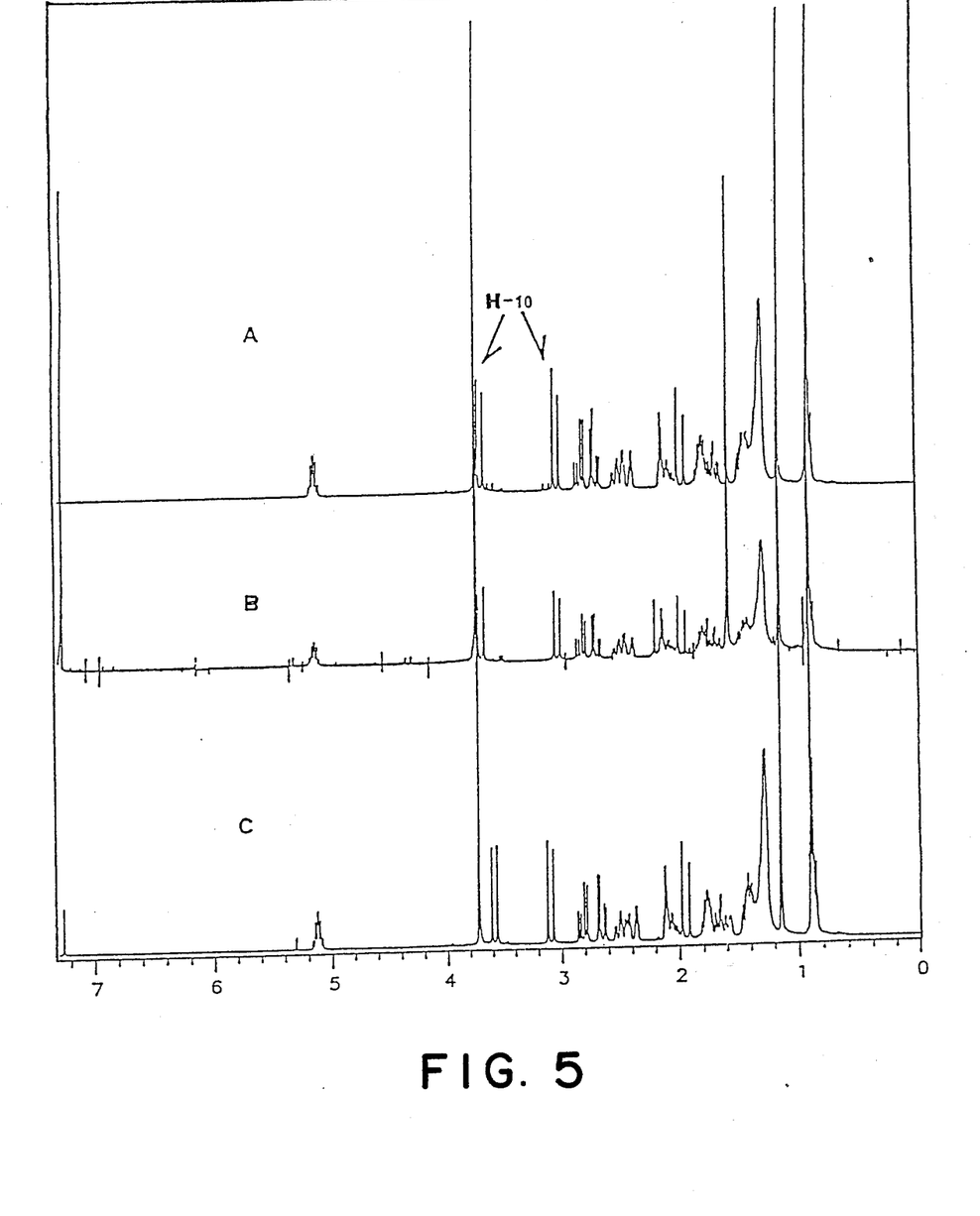
FIG. 5 shows $^1H$ NMR data of 3-[(+)—10-camphorsulfonyl]decanoic acid methyl ester, (A) 3-(R) synthetic (16a), (B) 3-(R) natural (14b), and (C) 3-(S) synthetic (16b), derivatives.

The preparation of optically pure synthetic methyl esters of 3-(R)- and 3-(S)-hydroxydecanoic acids 15a and 15b was carried out by separating an epimeric mixture of the (R)-methylbenzyl carbamates (Pirkle, W. H., J. R. Hauske [1977] J. Org. Chem. 42:2781) (17a and 17b) by HPLC using a phenyl bonded silica gel column. The isolated, optically pure carbamates were then cleaved with trichlorosilane to give methyl-3-(R)-hydroxydecanoate (15a) ([M]$_D$=−37.3°) and methyl-3-(S)-hydroxydecanoate (15b) ([M]$_D$=37.2°). The esters were converted to (+)-10-camphorsulfonates (16a and 16b) (Scheme III). $^1$H NMR spectra of the derivatives showed a very distinctive AB quartet for the C-10 position of the camphor moiety. The $^1$H NMR spectrum of 14b was superimposable on that of 16a (FIG. 5).

Therefore, the structure of 1 was determined as (R)-3-hydroxydecanoyl-L-Gln-L-Gln-L-Gln-didemnin B.

Didemnin Y (2), isolated as a minor component, showed a molecular ion at m/z 1795.0119 (M+H) and HRFAB mass spectra gave the molecular formula $C_{87}H_{139}N_{15}O_{25}$; 1 and 2 differ in molecular formula by $C_5H_8N_2O_2$, corresponding to a glutamyl unit. These data, along with $^1$H NMR spectra very similar to those of 1, suggest that the structure of 2 is 3-hydroxydecanoyl-L-Gln-L-Gln-L-Gln-L-Gln-didemnin B. This was confirmed by MS/MS, LR- and HRFABMS for the molecular ion of 2 and partially hydrolyzed compound 9 (Scheme IV). The stereochemistry at C-3 of the 3-hydroxydecanoyl moiety was determined analytically. Compound 2 (6 mg) was hydrolysed to give side chain fragment 9 (2.3 mg). FABMS and MS/MS data of 9 secured the sequence (Scheme IV). Acid hydrolysis of 9 (1 mg) followed by treatment with (R)-methylbenzylisocyanate gave the diastereomeric carbamate 10, whose retention time on HPLC (normal phase cyanocolumn) compared with those of synthetic carbamates indicated that the configuration at C-3 of 3-hydroxydecanoyl subunit was also R (Scheme V).

A three-day L1210 cell growth inhibition assay showed ID$_{50}$ 0.004 and 0.0064 ug/ml for 1 and 2, respectively, which are of the same magnitude as that of 4. The results are summarized in Table 1, supra.

Following are examples which illustrate procedures, including the best mode, for practicing the invention. These examples should not be construed as limiting. All percentages are by weight and all solvent mixture proportions are by volume unless otherwise noted.

Example 1 - Extraction and Initial Separation

Extraction and initial separation to obtain fraction A were done as follows: Tunicate sample AHCE #614 was collected on the southwest side of Long Cay, Lighthouse Reef, Belize, 17° 11.8' N by 87° 36.5' W at a depth of 50 to 100 feet. The sample was placed in 2-propanol and stored at $-10°$ C. until it was extracted by the procedure shown in Scheme I. A part of fraction A (18 g) was used to recover didemnins X and Y.

Isolation of didemnins. A part of fraction A (9 g) was partitioned between the lower and the upper phases of a mixture of ethyl acetate/heptane/methanol/water (7:4:4:3). Both lower and upper phases were concentrated to give solids (4.5 g each). A portion of the solid from the lower layer (1 g) was separated by CCC using toluene/ethyl acetate/methanol/water (6:7:7:4) as the solvent system with the lower phase being used as the mobile phase, at a flow rate of 2 mL/min at 600 rpm. A total of 40 fractions (24 mL each) were collected. The stationary phase was recovered from the first 10 fractions. Fraction 11 was concentrated in vacuo to give crude 8 (169 mg). Fractions 12 and 13 were combined, and the solvent was removed to give semipure 9 (416 mg). A portion of crude 8 was purified by successive C-18 reversed-phase gravity column chromatography and HPLC using a C-18 column with methanol/water (8:2) to give pure peptide 8 as a faint green solid (Rinehart, Gloer, Hughes et al. [1981], supra): mp 154°-164° C. (lit. [Rinehart, Gloer, Hughes et al., supra] mp 159°-161° C.); [alpha]$_D$ = −81.5° (c 0.4, CHCl$_3$) (lit. [Rinehart, Gloer, Hughes et al., supra] [alpha]$_D$ = −89.4°); $^1$H NMR (CDCl$_3$ delta 7.04 (2 H, d, J=8.4 Hz), 6.80 (2 H, d, J=8.4 Hz), 3.75 (3 H, s), 3.02 (3 H, s), 2.50 (3 H, s); HRFABMS calcd. for C$_{77}$H$_{118}$N$_{14}$O$_{23}$: 1607.8573 (M+H). Found: 1607.8590.

A semi-pure sample of didemnin E was purified by the procedure employed for 8 to give pure peptide 9 as a colorless solid: mp 158°-166° C. (lit. [Rinehart, Gloer, Hughes et al., supra] mp 164°-166° C.); [alpha]$_D$ = −84.6° (c 1.98, CHCl$_3$) (lit. [Rinehart, Gloer, Hughes et al., supra] [alpha]$_D$ = −90.6°); $^1$H NMR (CDCl$_3$) delta 7.05 (2 H, d, J=8.1 Hz), 6.80 (2 H, d, J=8.1 Hz), 3.76 (3 H, s), 3.10 (3 H, s), 2.51 (3 H, s); HRFABMS calcd. for C$_{72}$H$_{109}$N$_{12}$O$_{21}$: 1479.7987 (M+H). Found: 1479.7993.

Fractions 14-16 were combined to give 100 mg of a solid. A methanol soluble part of the solid, after filtration, was chromatographed on a gravity column packed with a NS gel with methanol to give 49.5 mg of a peptidal fraction. This was purified on HPLC using an amino column with methanol followed by a silica gel column with chloroform/methanol (3:1) to give pure peptide 2 (11.3 mg), amorphous; [alpha]$_D$ = −65° (c 0.93, CHCl$_3$-MeOH); IR (Neat) 3310, 2950, 1720, 1650 cm$^{-1}$; $^1$H NMR (CDCl$_3$-methanol-d$_4$) delta 7.30 (2 H, d, J=8.1 Hz), 6.70 (2 H, d, J=8.1 Hz), 3.74 (3 H, s), 2.98 (3 H, s), 2.49 (3 H, s); HRFABMS calcd. for C$_{87}$H$_{139}$N$_{15}$O$_{25}$: 1795.0145 (M+H). Found: 1795.0119.

Fractions 19-29 from the CCC separation were also combined to afford a light green solid (248 mg). This solid was separated by NS gel column chromatography using methanol to afford a peptidal solid. This material was passed through a Sep-Pak silica gel column which had been treated with ammonia gas with chloroform/methanol (4:1) to remove green pigments. The peptide was purified on HPLC using a silica gel column with chloroform/methanol (4:1) to give 1 (107 mg): solid; mp 156°-158° C.; [alpha]$_D$ = −88.6° (c 6.35, CHCl$_3$); IR (Neat) 3450, 3300, 2950, 1720, 1650 cm$^{-1}$; $^1$H NMR (CDCl$_3$-methanol-d$_4$) delta 7.02 (2 H, d, J=8.4 Hz), 6.78 (2 H, d, J=8.4 Hz), 3.72 (3 H, s), 3.00 (3 H, s), 2.47 (3 H, s); HRFABMS calcd. for C$_{82}$H$_{131}$N$_{13}$O$_{23}$: 1666.9559 (M+H). Found: 1666.9533.

Example 2 - Methanolysis of Didemnin X (1)

To a solution of 1 (122 mg) in 2 mL of methanol was added excess sodium carbonate (25 mg) with stirring at room temperature until TLC indicated the starting material had been consumed (0.5 hr). The reaction mixture was filtered, and concentrated to give a mixture of methanol-soluble products. The solid was dissolved in DMSO and filtered to remove the residual salts. Removal of the DMSO by a stream of nitrogen gave a colorless solid 13 (35 mg): [alpha]$_D$ = 19° (c 0.14, DMSO); LR- and HRFABMS see Scheme II. The methanol-soluble portion was filtered to remove residual solid, then further separated on reversed-phase HPLC using a C-18 column with methanol/water (4:1) to give a major component along with five minor compounds. The major product was re-chromatographed to give a pure solid 12: mp 152°-156° C.; $^1$H NMR (CDCl$_3$) see FIG. 3; HRFABMS calcd. for C$_{57}$H$_{89}$N$_7$O$_{15}$: 1112.6495 (M +H). Found: 1112.6502.

Example 3 - GC Analysis of Hydrolyzed 1, 3, 4, and 9

A sample of 1 (3 mg) was heated with 0.5 mL of 6N HCl at 110° C. for 21 hours. Dichloromethane was added to the mixture and the aqueous phase was evaporated to dryness. The residual material was treated with a mixture of methanol/acetyl chloride (10:1) at 110° C. for 0.5 hr. The solvent was removed with a stream of nitrogen gas, and the resulting oil was then treated with trifluoroacetic anhydride/trifluoroacetic acid (0.2 mL, each) at 110° C. for 4 minutes. Excess acid was removed with a stream of nitrogen gas, and the residue was dissolved in 1 mL of dichloromethane for GC analysis. Samples of hydrolyzed 3, 4, and 9 were prepared by the same procedure.

Example 4 - Hydrolysis of 13 with 3N HCl

Compound 13 (12.3 mg) was dissolved in 3N HCl (1 mL) and heated at 120° in a sealed sample vial for 8 hours. The mixture was extracted with dichloromethane (2×1 mL), the organic layer was dried over sodium sulfate, and the solvent was removed to give 14 as a white solid: $^1$H NMR (CDCl$_3$) delta 4.03 (1 H, br s), 2.55 (1 H, br d, J=17.7 Hz), 2.45 (1 H, dd, J=17.1 Hz), 1.63-1.38 (2 H, m), 1.25 (br s), 0.88 (br t, J=5.7 Hz); HRFABMS calcd. for C$_{10}$H$_{20}$O$_3$: 189.1491 (M+H). Found: 189.1486. HREIMS calcd. for C$_3$H$_5$O$_3$: 89.023886. Found: 89.023886. This compound was then treated with a mixture of methanol/acetic anhydride (9:1) for 30 minutes at 120° C. in a sealed vial. The solvent was removed with a stream of nitrogen. The residual material was separated on a silica Sep-Pak column with dichloromethane/ethyl acetate (5:1) to give 0.89 mg of 14a as an oil: $^1$H NMR (CDCl$_3$) delta 4.00 (1 H, m), 3.71 (3 H, s), 2.46 (1 H, dd, J=3.3, 16.5 Hz), 2.40 (1 H, dd, J=9.0, 16.8 Hz), 1.54-1.34 m, 1.28 br s, 0.88 (3 H, t, J=6.3 Hz).

Example 5 - Synthesis of (R,S)-3-Hydroxydecanoic Acid and its Methyl Ester

Octanyl chloride (16.2 g, 0.088 mol) was added to a solution of 2,2-dimethyl-1,3-dioxane-4,6-dione (11.5 g, 0.080 mol) in dichloromethane (100 mL) and pyridine (12.8 mL) at 0° C. over 10 minutes. The reaction mixture was stirred for 1 hour at room temperature. The reaction product was partitioned successively between dichloromethane, and aqueous HCl (10%), and then water. The organic portion was concentrated to give a deep red oil and then refluxed with methanol (250 ml) for 12 hours. The product was purified by silica gel gravity column chromatography (dichloromethane) to give a light yellow oil (14.6 g). A part of the oil (650 mg) was dissolved in THF (10 mL). To the solution was added a suspension of sodium borohydride (120 mg, 3.2 mmol) and water (1 mL) at 0° C. with stirring for 1 hour. The reaction was quenched by adding acetone (5 mL), the solvent was removed in vacuo, and the residual material was triturated with dichloromethane. The organic solubles were purified by silica gel gravity column chromatography with dichloromethane/ethyl acetate (3:1) to give (R,S)-methyl-3-hydroxydecanoate as an oil: $^1$H NMR, identical with that of 14a; $^{13}$C NMR (CDCl$_3$) delta 173.79, 67.92, 51.50, 41.17, 36.52, 31.74, 29.42, 29.17, 25.44, 22.58, 14.00. A mixture of the methyl ester (166 mg, 0.82 mmol) with 6N sodium hydroxide was heated at 110° C. for 1 minute. The saponified material was dissolved in water (1 mL) and the pH of the solution was adjusted to 1 by adding 6N HCl. Dichloromethane was added to the solution, and the organic layer was dried over sodium sulfate. The solvent was removed in vacuo to give 127 mg (83%) of 15 as fine crystals: mp 74° C.; $^1$H NMR (CDCl$_3$), identical with that of 14.

Example 6 - Conversion of (R,S)-methyl-3-hydroxydecanoate to its (+)-10-camphorsulfonate 16a and 16b A mixture of (R,S)-methyl-3-hydroxydecanoate (87 mg, 0.43 mmol) and (+)-10-camphorsulfonyl chloride (125 mg, 0.499 mmol) dissolved in pyridine (0.5 mL) was allowed to stand at room temperature for 12 hours. Pyridine was removed in vacuo, and the residual oil was subjected to gravity silica gel column chromatography with chloroform/ethyl acetate (9:1) to give 132 mg of an epimeric mixture (73%) of 16a and 16b as an oil: $^1$H NMR (CDCl$_3$), see FIG. 4.

Example 7 - Conversion of 14a to (+)-10-Camphorsulfonate, 14b

A mixture of ester 14a (0.89 mg), (+)-10-camphorsulfonyl chloride (4.6 mg), and pyridine (0.2 mL) was allowed to stand at room temperature for 12 hours, then pyridine was removed with a stream of nitrogen. The resulting oil was passed through a silica gel Sep-Pak column with dichloromethane/ethyl acetate (5:1) then purified by HPLC using a cyano analytical column with hexane/2-propanol (20:1) to give 0.95 mg of an oil: $^1$H NMR (CDCl$_3$), identical with that of 16a; see FIG. 5.

Example 8 - Reaction of (R,S)-methyl-3-hydroxydecanoate with (R)-alpha-methylbenzyl isocyanate A mixture of (R)-alpha-methylbenzyl isocyanate (668 mg, 4.5 mmol) and (R,S)-methyl-3-hydroxydecanoate (850 mg, 4.2 mmol) was dissolved in dichloromethane (2 mL) and pyridine (0.5 mL), and refluxed for 42 hours. The solvent was removed in vacuo, and the resulting oil was purified by gravity column chromatography using silica gel with hexane/2-propanol (20:1) to give 1.19 g of a mixture of carbamates 17a and 17b (78%) as an oil: CIMS (M+H, methane) m/z (rel. intensity) 350.2 (100), 334.2 (12), 318.2 (8), 272.2 (2), 246 (43), 233.1 (37), 203.2 (43), 185.2 (95), 164.1 (60), 153.1 (33), 120.1 (40), 105.1 (80), 85.0 (35), 71.1 (30), 59.1 (38). A mixture of 17a and 17b (70 mg) was separated on HPLC, using a phenyl column with hexane/2-propanol (60:1), to afford 28 mg of optically pure carbamate 17a as the less polar isomer: $^1$H NMR (CDCl$_3$) delta 7.30 (5 H, m), 5.07 (1 H, m), 4.95 (1 H, br d, J=6 Hz), 4.92 (1 H, br m), 3.68 (3 H, s); [alpha]$_D$=33.8° (c 2.80, CHCl$_3$). The more polar fraction gave 29 mg of the other optically pure carbamate 17b: [alpha]$_D$=36.6° (c 2.88, CHCl$_3$); $^1$H NMR (CDCl$_3$) delta 7.30 (5 H, m), 5.06 (1 H, m), 4.95 (1 H, br d), 4.88 (1 H, br m), 3.56 (3 H, s).

Example 9 - Cleavage of Carbamates 17a and 17b to Give Optically Pure Esters 15a and 15b To a solution of 17b (22.5 mg) in 1 mL of dried benzene was added 20 uL of triethylamine and 25 ul of trichlorosilane. The mixture was stirred for 36 hours at room temperature, then saturated aqueous ammonium chloride (1 mL) was added. The organic layer was dried over sodium sulfate, and the solvent was removed with a stream of nitrogen. The resulting material was purified by HPLC using a cyano column with hexane/ethyl acetate (4:1) to give 4.4 mg (33%) of optically pure S ester 15b as an oil; [M]$_D$=37.2° (c 0.243, CHCl$_3$). The other isomer (24.2 mg) 17a was cleaved by the same procedure to give 7.05 mg (54%) of pure R ester 15b as an oil; [M]$_D$=−37.2° (c 0.565, CHCl$_3$), (lit. [Parker, W. L. and M. L. Rathnum (1975) J. Antibiot. 28:379], [M]$_D$=−37°).

Example 10 - Reaction of Optically Pure Esters 15a and 15b with (+)-10-Camphorsulfonyl Chloride A mixture of (S)-ester 15b (1.89 mg) and (+)-10-camphorsulfonyl chloride (11.5 mg) was dissolved in pyridine (0.5 mL) and allowed to stand at room temperature for 5 hours. Pyridine was removed with a stream of nitrogen, and the residual material was separated by silica gel Sep-Pak column chromatography with dichloromethane/ethyl acetate (5:1). The resulting oil was purified on HPLC using a cyano column with dichloromethane/ethyl acetate (5:1) to give pure sulfonate 16b as an oil: $^1$H NMR (CDCl$_3$) delta 5.12 (1 H, ddt, J=6.1, 6.1, 6.1 Hz), 3.72 (3 H, s), 3.59 (1 H, d, J=15.0 Hz), 3.09 (1 H, d, J=15.0 Hz). The (R)-ester 15a was converted to the corresponding (+)-10-camphorsulfonate by using the same procedure to give 16a as an oil: $^1$H NMR (CDCl$_3$) delta 5.12 (1 H, ddt, J=6.1, 6.1, 6.1 Hz), 3.72 (3 H), 3.67 (1 H, d, 15.0 Hz), 3.01 (1 H, d, 15.0 Hz).

Example 11 - Salts of Didemnins

Since the didemnins are weakly basic, they form salts with mineral acids such as HCl, H$_2$SO$_4$, and H$_3$PO$_4$. Such salts can be prepared by suspending the didemnins in water, adding a dilute acid until the pH of the solution is about 3 to 4, and freeze-drying the solution to provide a dried residue of the didemnin salt.

Example 12 - Derivatives of Didemnins

The didemnins of the invention have and hydroxyl groups available for derivatization. Thus, acyl esters of the didemnins can be prepared by methods well known to those skilled in the art. Acyl derivatives of the didemnins can be used for the same biological purposes as the parent compounds.

Acids which can be used in the acylation of a didemnin are as disclosed in U.S. Pat. No. 4,548,814, Columns 3 and 4. The administration of didemnins X and Y can be carried out as disclosed in U.S. Pat. No. 4,548,814, Columns 9 through 15. This patent is incorporated herein by reference thereto for the above-noted disclosures.

Scheme III.

(1) Parker, W. L. and Rathnum, M. L., J. Antibiot. 28, 379–389, (1975)

Scheme IV.

(a) FABMS fragmentation pattern and MS/MS data of didemnin Y (2)

didemnin Y (2), m/z 1795.0199 (M + H), $C_{87}H_{140}N_{15}O_{25}$

| fragment # | mass observed[a] | formula |
|---|---|---|
| A | 816.7($H_2$) | |
| B | 943.5765 Δ −4.5 mmu, | $C_{49}H_{77}N_6O_{12}(H_2)$ |
| C | 1040.6247, Δ −3.7 mmu | $C_{54}H_{84}N_7O_{15}(H_2)$ |
| D | 1112.6483, Δ −1.2 mmu | $C_{57}H_{88}N_7O_{15}(H_2)$ |
| E | 1240.7121, Δ 0.4 mmu | $C_{62}H_{96}N_9O_{17}(H_2)$ |
| F | 1368.7($H_2$) | |
| G | 1496.6($H_2$) | |
| A' | 979.7 | |
| C' | 755.4 | |
| D' | 701.3811, Δ −2.3 mmu | $C_{30}H_{51}N_8O_{11}(H_2)$ |
| E' | 555.3147, Δ 0.5 mmu | $C_{25}H_{43}N_6O_6$ |
| F' | 427.2 | |
| G' | 299.2 | |

(b) Fab MS/MS data of side chain fragment (9) of didemnin Y (2)

-continued
Scheme IV.

compound 9 (M + H) = 701.1

| fragment # | mass | fragment # | mass |
|---|---|---|---|
| A | 684 | B' | 147(H$_2$) |
| B | 555 | C' | 275(H$_2$) |
| C | 427 | D' | 403(H$_2$) |
| D | 299 | E' | 531(H$_2$) |
| E | 188(H$_2$) | | | a Low resolution data were obtained from MS/MS (FAB) experiment.

Scheme V
Absolute stereochemistry of 3-hydroxydecanoyl unit of didemnin Y (2)

Didemnin Y (6.0 mg) $\xrightarrow[\text{MeOH}]{K_2CO_3}$ Fragment B (2.3 mg, 98%)

1. 6 N HCl, 12 h, 100° C.
2. partition

Organic / Aqueous
Aqueous: Chiral GC Analysis → L-Glutamic acid

HPLC (Cyano Anal.)
Retention
Synthetic R,S: 10.4 min
Synthetic R,R: 12.6 min
Natural: 12.6 min benzene/TEA

Naturally derived Carbamate

HRCIMS (M + H) 350.2330703
C$_{20}$H$_{32}$NO$_4$, Δ0.1 mmu

CIMS 350.2, 246.1, 203.1, 185.1 etc.
(identical with that of synthetic sample)

We claim:
1. A didemnin of the formula wherein R = or wherein R =

2. Didemnin X, according to claim 1, wherein R= or or the acid addition salts thereof or esters resulting from acylation of the alcohol groups.

3. Didemnin Y, according to claim 1, wherein R= or the acid addition salts thereof or esters resulting from acylation of the alcohol groups.

4. A process for treating animals and humans hosting a neoplastic disease which comprises administering to said host in need of treatment an effective neoplastic disease inhibiting amount of a didemnin compound of the formula -continued wherein R =

5. A process, according to claim 4, wherein said didemnin compound is didemnin X, having the formula 6. A process, according to claim 4, wherein said didemnin compound is didemnin Y, having the formula wherein R =

Scheme IV.

(a) FABMS fragmentation pattern and MS/MS data of didemnin Y (2)

didemnin Y (2), m/z 1795.0199 (M + H), $C_{87}H_{140}N_{15}O_{25}$

| fragment # | mass observed[a] | formula |
|---|---|---|
| A | 816.7($H_2$) | |
| B | 943.5765 Δ −4.5 mmu, | $C_{49}H_{77}N_6O_{12}(H_2)$ |
| C | 1040.6247, Δ −3.7 mmu | $C_{54}H_{84}N_7O_{15}(H_2)$ |
| D | 1112.6483, Δ −1.2 mmu | $C_{57}H_{88}N_7O_{15}(H_2)$ |
| E | 1240.7121, Δ 0.4 mmu | $C_{62}H_{96}N_9O_{17}(H_2)$ |
| F | 1368.7($H_2$) | |
| G | 1496.6($H_2$) | |
| A' | 979.7 | |
| C' | 755.4 | |
| D' | 701.3811, Δ −2.3 mmu | $C_{30}H_{51}N_8O_{11}(H_2)$ |
| E' | 555.3147, Δ 0.5 mmu | $C_{25}H_{43}N_6O_6$ |
| F' | 427.2 | |
| G' | 299.2 | |

(b) Fab MS/MS data of side chain fragment (9) of didemnin Y (2)

compound 9 (M + H) = 701.1

| fragment # | mass | fragment # | mass |
|---|---|---|---|
| A | 684 | B' | 147($H_2$) |
| B | 555 | C' | 275($H_2$) |
| C | 427 | D' | 403($H_2$) |
| D | 299 | E' | 531($H_2$) |
| E | 188($H_2$) | | | a Low resolution data were obtained from MS/MS (FAB) experiment.

-continued

-continued

* * * * *